United States Patent [19]

Connell, Jr. et al.

[11] 4,149,419
[45] Apr. 17, 1979

[54] ULTRASONIC TRANSDUCER PROBE

[75] Inventors: Raymond S. Connell, Jr.; John M. Santacroce, both of San Jose, Calif.

[73] Assignee: Smith Kline Instruments, Inc., Sunnyvale, Calif.

[21] Appl. No.: 854,902

[22] Filed: Nov. 25, 1977

[51] Int. Cl.² ............... G01N 29/04; A61B 10/00
[52] U.S. Cl. ............... 73/621; 73/626; 73/639; 73/644; 128/2 V
[58] Field of Search ............... 73/639, 641, 626, 621, 73/633, 634, 625, 644; 128/2 V, 205 Z

[56] References Cited

U.S. PATENT DOCUMENTS

| | | | |
|---|---|---|---|
| 3,130,577 | 4/1964 | Cowan | 73/633 |
| 3,423,991 | 1/1969 | Collins | 73/639 |
| 3,714,817 | 2/1973 | Miller | 73/639 |
| 3,779,234 | 12/1973 | Eggleton et al. | 128/2 V |
| 3,927,661 | 12/1975 | Takemura | 73/621 X |
| 4,034,744 | 7/1977 | Goldberg | 128/2 V |

*Primary Examiner*—James J. Gill

[57] ABSTRACT

An ultrasonic transducer probe having a sealed rotor housing, a plurality of transducers mounted on a rotor disposed in said housing. A rotor shaft mounts the rotor and extends through the housing. A drive assembly including commutating and position indicating means receives said housing and rotor shaft and serves to drive the rotor, commutate electrical energy to and from said transducers and indicate the angular position of said rotor. A handle including means for driving said drive assembly is attached to said drive assembly to position the rotor housing and drive assembly against the body the rotate said rotor to cause the transducers to scan a sector of the body.

8 Claims, 10 Drawing Figures

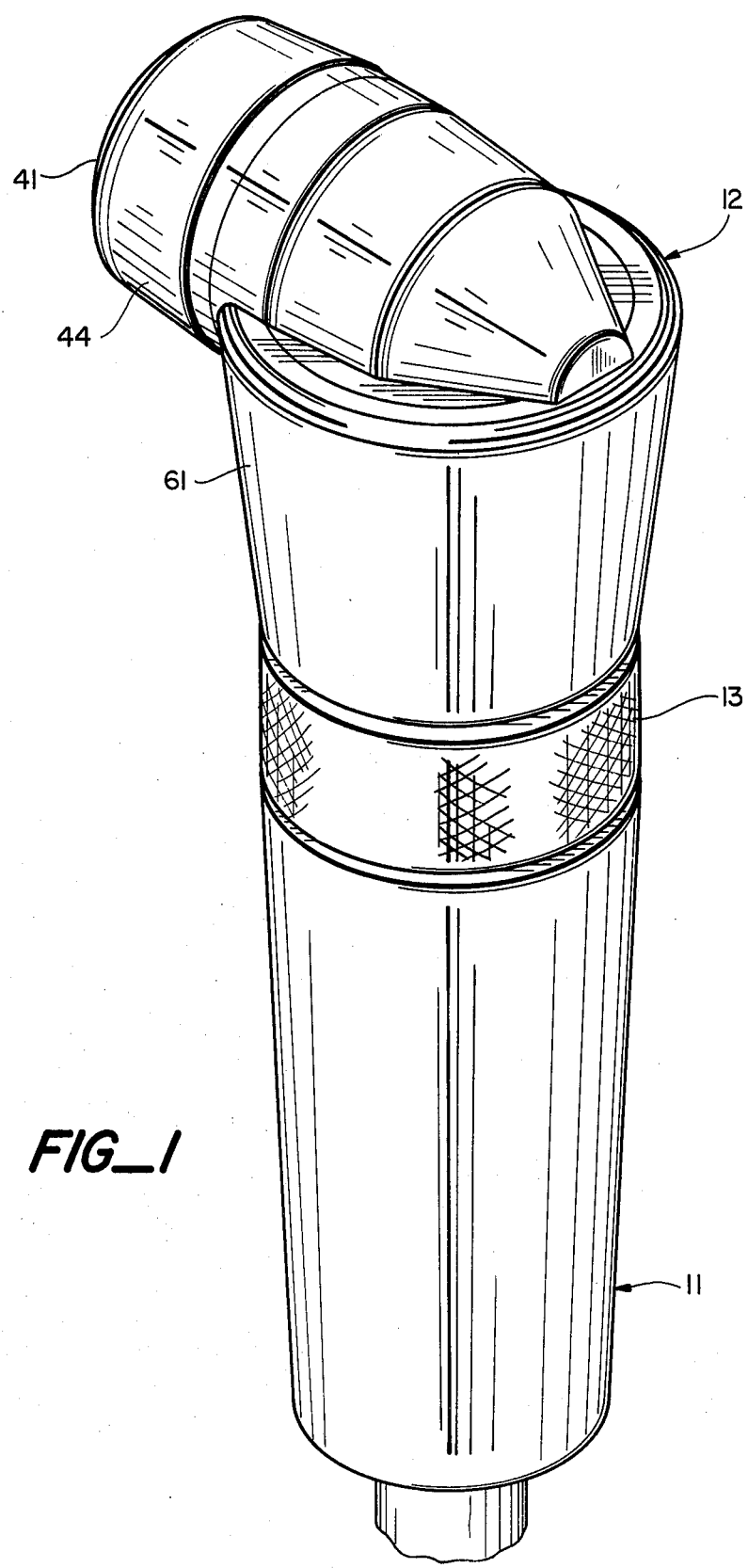
FIG_1

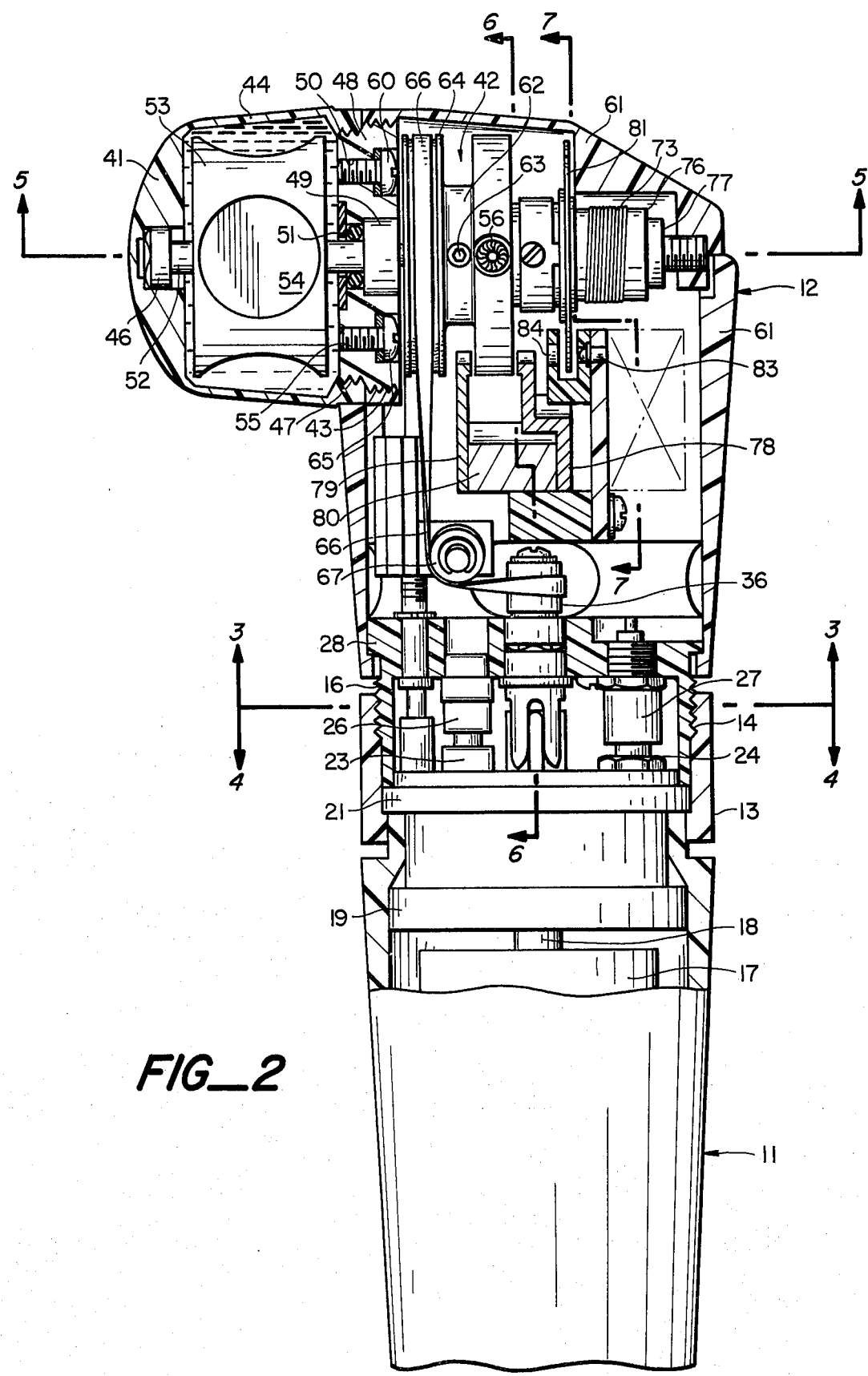
FIG_2

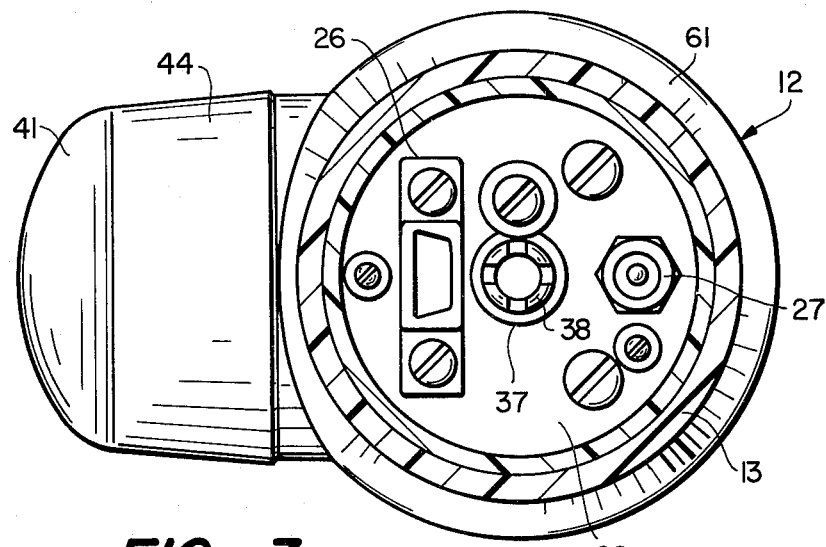
FIG_3
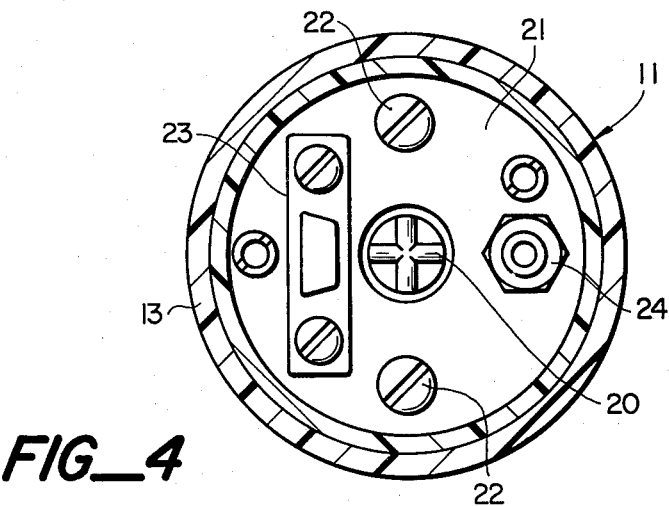
FIG_4
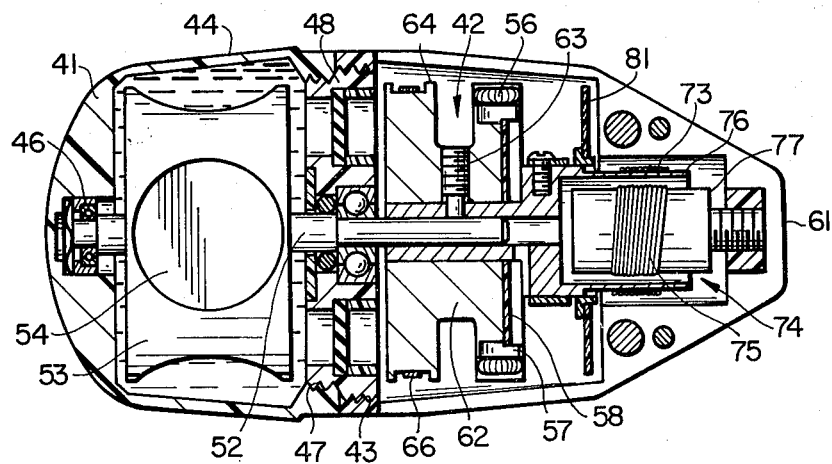
FIG_5

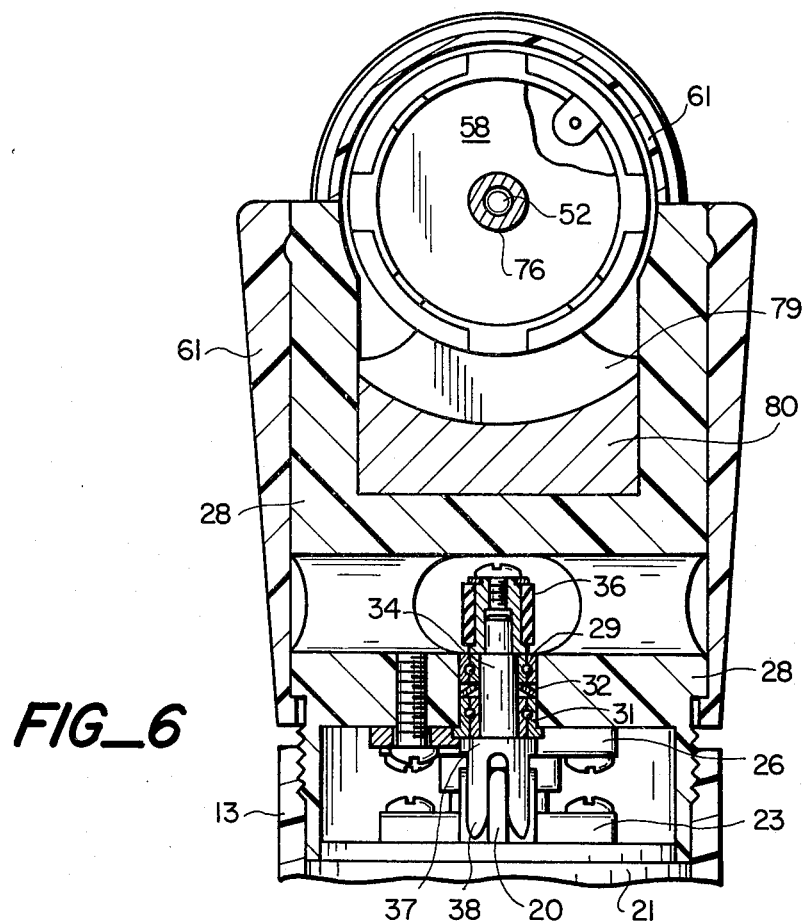
FIG_6
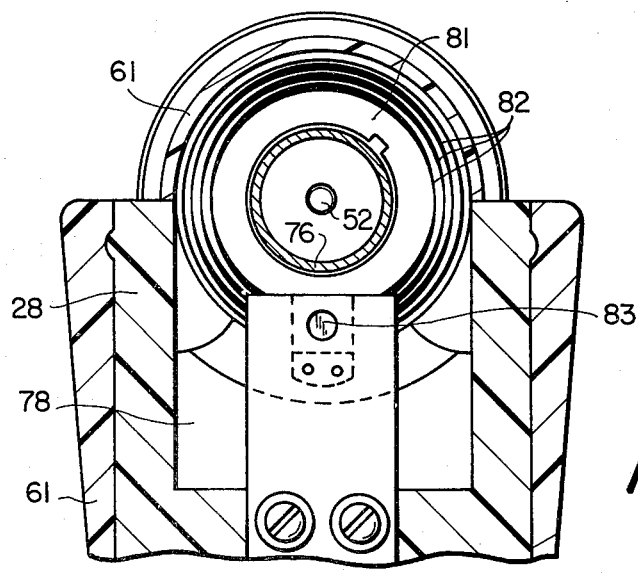
FIG_7

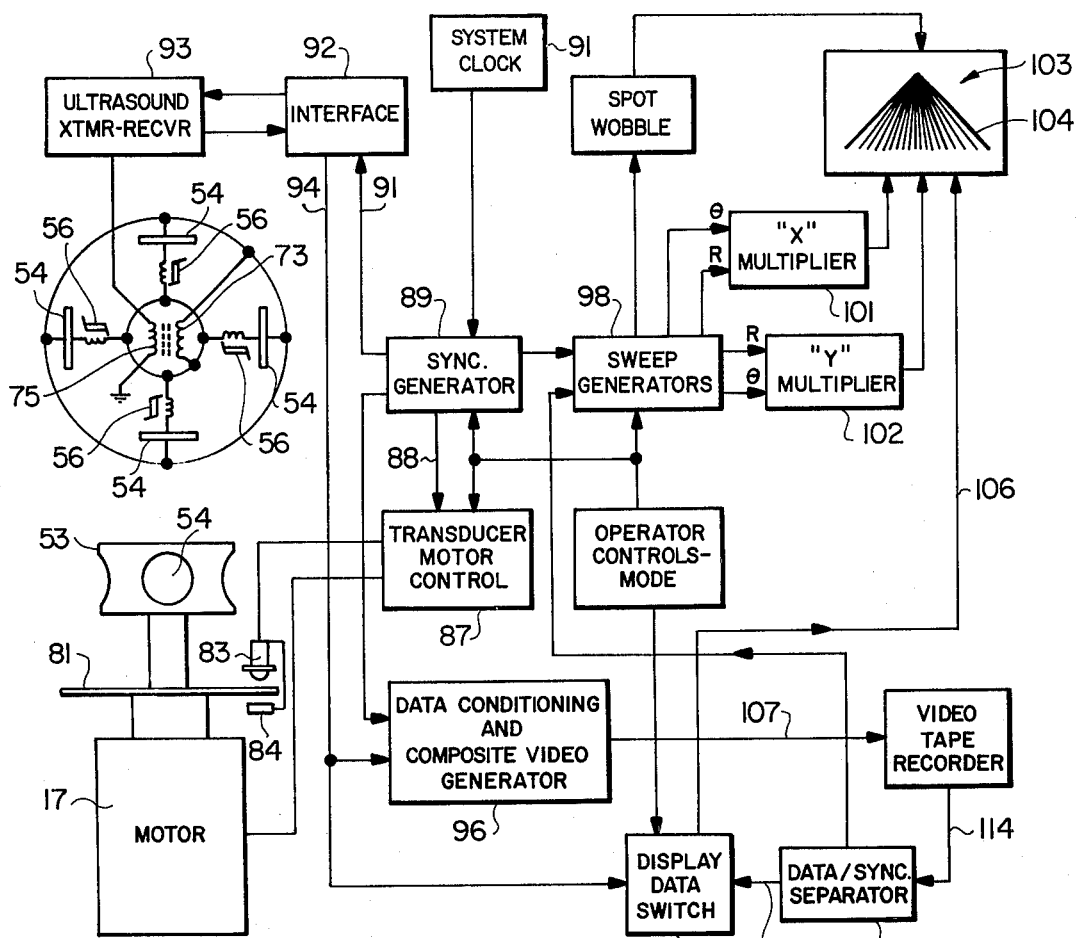
FIG_8
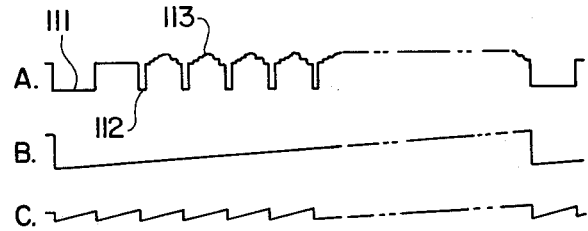
FIG_9
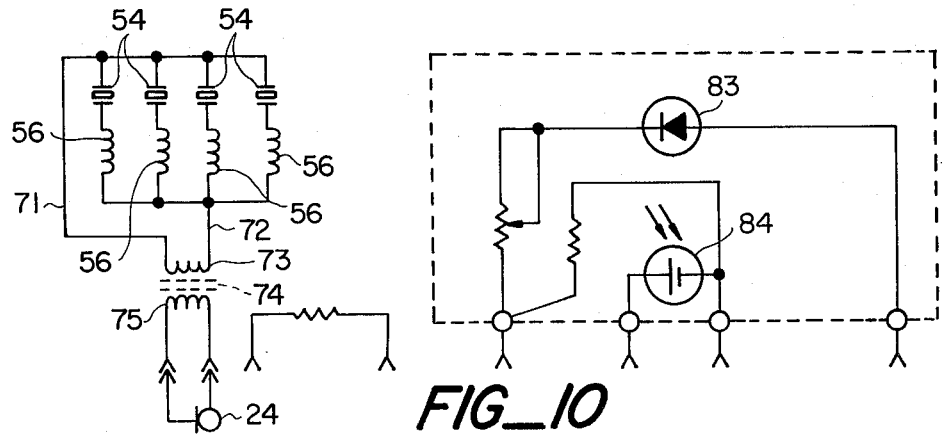
FIG_10

ULTRASONIC TRANSDUCER PROBE

BACKGROUND OF THE INVENTION

This invention relates generally to an ultrasonic transducer probe for use in transmitting and receiving ultrasonic energy to and from a body being scanned and more particularly to a probe suitable for use in an ultrasonic sector scanning system.

In recent years, ultrasonic scanning of regions of the human body have found wide applications. Among advantages of such scanning systems is that the energy required is low, thereby reducing the possibility of injury to a patient. There are no radiation side effects. The body is not invaded.

As is known, in such systems the ultrasound energy is transmitted in a beam of pulses each followed by a relatively long interval where no transmission occurs. During this interval the pulse energy is transmitted through the body. Whenever a pulse of energy strikes a boundary between two substances having different acoustic impedance, a portion of the ultrasound energy is reflected. Some of the reflected energy returns as an echo to the transmitting transducer. The beam produces additional echoes from deeper interfaces. The crystals which serve as transmitting transducers also serve as receiving transducers to convert the reflected ultrasound energy into electrical signals. These signals are amplified and displayed as static or dynamic patterns on a cathode ray tube. The relative position of the interfaces in the body are displayed.

A particular type of scanner used is a sector scanner. A sector scanner generally comprises an ultrasonic transducer (piezoelectric element) which is mounted to be driven. The drive moves the transducer, generally in the form of a flat circular object, back and forth in an arc scanning motion. During this process the transducer is pulsed with high voltage pulses at pulse repetition rates in the order of 3000 Hz. These pulses cause the piezoelectric element to mechanically ring thereby emitting high frequency sound waves in a beam. As the transducer scans, it forms a plurality of beams in a fan or sector shape. The beams impinge upon the structure within the body and when differences in acoustic impedance exist, energy is partially reflected back to the transducer element to cause the transducer to mechanically vibrate. At this point, the transducer element acts like a receiver and converts these mechanical vibrations to electrical energy. This energy is amplified and processed so that it can be displayed on a cathode ray tube.

The mechanical driving arrangement not only drives the transducer but also includes means for generating an electrical output representative of transducer position. The electrical output from the driving arrangement is processed and utilized to create horizontal and vertical signals to drive the vertical and horizontal deflection circuits of a cathode ray tube. The signals from the ultrasonic transducer are used to control the intensity of the cathode ray tube beam. The resultant image is a sector shaped representation of the internal organs of the body.

Another prior art system which allows real time examination of internal organs of the body such as the heart employs a catheter which has a rotating tip with a plurality of transducers. The transducers are selectively connected to a pulser to transmit ultrasonic sound into the body and to receive echoes therefrom. The echo pulses are processed and applied to a cathode ray tube whereby to provide sequential representations of the area at a rate which is dependent on the speed of rotation of the transducers and with a resolution which is dependent upon the pulse rate.

In copending application Ser. No. 807,438, entitled "Ultrasonic Transducer Probe" and assigned to the same assignee, there is described a rotary transducer probe including a head adapted to house drive means including bevel gears, commutating means including sliding contacts and position sensing means in the form of a light source and photodiode. Although the probe described in said copending application is satisfactory, the drive means introduces some jitter due to the engagement of the bevel gear teeth. The sliding contacts are subject to wear.

OBJECTS AND SUMMARY OF THE INVENTION

It is a general object of the present invention to provide an improved ultrasonic transducer probe.

It is another object of the present invention to provide a probe including transducers mounted on a belt driven rotor mounted in a sealed housing.

It is a further object of the present invention to provide an ultrasonic transducer probe which efficiently couples ultrasonic energy between the transducers and the body being examined.

It is a further object of the present invention to provide a continuous position sensing of a transducer rotor so that the transducer position may be accurately controlled by a servo system.

It is a further object of the present invention to provide an ultrasonic transducer probe which includes a rotor having a plurality of transducer elements mounted on a rotor disposed in a sealed housing and rotary transformer means for electrically coupling electrical energy to and from said transducers.

It is another object of the present invention to provide an ultrasonic transducer probe including a plurality of transducers mounted on a rotor and saturable reactors for selectively connecting said transducers to associated electrical circuits.

It is still another object of the present invention to provide an ultrasonic transducer probe including a rotor disposed in a sealed housing filled with a fluid for coupling energy between the transducers and the body to which the housing is applied with the housing configured to minimize the effect of ultrasound energy reflected from the housing walls.

The foregoing and other objects of the invention are achieved by a probe which includes a rotor housing, a rotor having a plurality of transducers disposed thereon mounted for rotation within said housing and including a shaft extending from said housing, a drive assembly including commutating and position indicating means adapted to receive said housing and drive said rotor, couple electrical energy to and from said transducers and indicate the position of the rotor, and means adapted to be detachably secured to said drive assembly to drive the rotor.

BRIEF DESCRIPTION OF THE DRAWINGS

FIG. 1 is a perspective view showing an ultrasonic transducer probe in accordance with the present invention.

FIG. 2 is a view, partly in section, showing the transducer probe assembly of FIG. 1.

FIG. 3 is a sectional view taken generally along the line 3—3 of FIG. 2.

FIG. 4 is a sectional view taken generally along the line 4—4 of FIG. 3.

FIG. 5 is a sectional view taken generally along the line 5—5 of FIG. 2.

FIG. 6 is a sectional view taken generally along the line 6—6 of FIG. 2.

FIG. 7 is a sectional view taken generally along the line 7—7 of FIG. 2.

FIG. 8 is a block diagram of an electrical system suitable for use in connection with the probe of FIGS. 1-7.

FIG. 9 is a timing diagram showing the waveforms at various portions of the system of FIG. 8.

FIG. 10 is a schematic circuit diagram illustrating the transducers, the rotary transformer and saturable reactors and the position sensing means.

DESCRIPTION OF PREFERRED EMBODIMENTS

Referring to FIG. 1, the probe includes a handle 11 which is detachably secured to a scanning head designated generally by the numeral 12 by means of a ring 13 which has threads 14 adapted to engage threads 16 formed on the end of the head 12, FIG. 2. The handle houses a motor 17 suitably mounted therein and having a shaft 18 extending through and journalled to the round block 19 secured to the end of the handle 11. The block 19 is held in place by means of a circular plate 21 and screws 22, FIGS. 2 and 4. The shaft engages and drives the cross-shaped coupler 20. The block 19 also serves to securely mount electrical connectors 23 and 24 which are adapted to engage the female connectors 26 and 27 supported on the threaded block 28 mounted at the end of the head 12. The block 28 includes spaced bearings 29 and 31 with a beveled spring 32 which urges them apart, FIG. 6. The bearings receive shaft 34. A pulley 36 is mounted at one end of the shaft. The other end of the shaft includes a coupler 37 having two slots forming four fingers 38 which extend into and engage with the cross-like member 20. Thus, energization of the motor in the handle serves to rotate the pulley 36 in the end of the head.

Thus, the handle includes means for attaching the handle to the head and providing mechanical connection between the head and driving motor and electrical connection between equipment associated with the handle and the head for purposes to be presently described.

The scanning head includes a rotary transducer housing 41 and a drive assembly 42. The transducer housing 41 is detachably secured to the drive assembly by threads 43. The housing includes an outer conical shaped shell 44 which has a taper of about 5°. The shell end mounts a bearing 46 at its end and includes threads 47 at the other end to receive a plug 48. The plug 48 carries a bearing 49 and seal 51.

A rotor shaft 52 has one end mounted in bearing 46 and its other end extends through the bearing 49. The shaft mounts a rotary transducer assembly including rotor 53 adapted to mount a plurality of transducers 54, in this instance, four such transducers at 90°. The outer surface of each transducer is concave to provide a focusing action for the emitted ultrasonic energy. The plug includes threaded openings 50 and 55 which receive sealing screws 60 and 65 and provide for filling the interior of the housing with an ultrasound transmitting fluid such as ethylene glycol and water. This solution substantially matches the body impedance whereby the ultrasound energy travels efficiently to and from the body. The cup-shaped housing walls are inclined at an angle or tapered with respect to the transducers to minimize reverberations due to reflection of energy from the walls. The wall thickness is substantially one-half wavelength at the ultrasound frequency to increase transmission. The outer and inner surfaces of the wall have common centers whereby the emitted and received ultrasound energy is not refracted.

The drive assembly includes a housing 61 which houses the drive and the commutating and positioning means. The drive includes a spool 62 which is secured to the shaft 52 by means of a set screw 63, FIG. 5. One end of the spool includes a pulley 64 adapted to receive belt 66 which extends towards the handle over spaced idler pulleys 67 and over the driven pulley 36 previously described. Thus, when the motor is energized, it serves to drive the belt to rotatably drive the spool and, in turn, drive the shaft 52 and rotor 53 with its transducers 54. The other end of the spool includes a housing for a plurality of saturable reactors 56 which are spaced equally around the periphery thereof and held in place in notches 57 by means of a plate 58 secured to the pulley face. The saturable reactors are connected in series one to each of the transducers as more clearly shown in FIG. 10. The other end of the transducers and the other end of the saturable reactors are connected in common to the lines 71 and 72, respectively. The lines 71 and 72 are connected to the ends of the primary winding 73 of transformer 74 as shown.

The primary winding 73 of the transformer is mounted on the outside of a hollow member 76 and rotates with the shaft and rotor. A stationary secondary winding 75 is mounted in drive housing on a cylinder 77. It is mounted within the hollow member to be coupled to winding 73 and has its leads extending outwardly to the connector 24. The windings 73 and 75 form a rotary transformer which couple electrical signals into and out of the transducers.

In accordance with the present invention, there is provided a permanent magnet 80 which includes a pair of spaced pole pieces 78 and 79 which straddle the toroid mounting member. The ends of the pole pieces extend approximately 90° around the circumference. As each saturable reactor 56 comes into the magnetic field produced between the pole pieces, its reluctance is reduced and signals can pass freely between the transducers through the winding 75. In this way signals coupled to the secondary of the transformer are coupled from the primary through the saturable reactor having low reluctance to the associated ultrasonic transducer. Preferably, the magnet extends over an angle somewhat less than the switching arc to minimize switching overlap between transducers. For example, if four transducers are employed, the magnet arc is 90° less approximately 7° to provide a scan angle of substantially 83°.

The drive head also includes means for generating signals indicative of the position of the rotary transducer whereby to provide signals to a servo control. Preferably, the output signals are of a triangular waveshape. The signals are generated by means of a transparent disc 81 which has a plurality of concentric opaque rings 82 formed thereon as by photoetching. The rings 82 vary in thickness from substantially zero thickness to substantially full thickness, FIG. 7. Associated with the transparent disc 81 is a light source 83 and a photodetector 84 disposed on opposite sides. Thus, the signals from the photodetector will be maximum when the thin portions of the circles intercept the light, while they will be minimum when the thick portions of the circles intercept the light to give a triangular waveshaped signal.

Thus, it is seen that there has been provided a transducer probe including a plurality of ultrasonic transducers mounted upon a rotor in a transmitting fluid and rotating in a plane substantially parallel to a plane through the axis of the handle. The rotary probe is driven by a belt providing a smooth drive. Means are provided for commutating signals between a rotary transformer and the transducers thereby eliminating the need for contacts and switches. A position sensing disc is provided which gives an output electrical wave of triangular waveshape.

The transducer is schematically shown in FIG. 8 connected to an electrical system for providing the motor control signals and the sensor display.

The output of the phototransducer 84 is applied to a motor control 87 to which is also applied a reference frequency along the line 88 from sync generator 89 which serves to synchronize the operation of the overall system as will be presently described. Input to the sync generator is from a system clock 91 which may include a crystal together with appropriate dividers to provide a control frequency to the sync generator 89. The output of the line 88 may, for example, be a 60 Hertz output which is applied to the motor control. The output pulses from the phototransducer 84 are employed in a servo system to servo control operation of the motor 17 and to control the position of the rotor 53 whereby the position of the transducer is accurately determined as the rotor rotates. Ultrasonic pulses are applied sequentially to the individual transducers at a high rate so that they scan a plurality of lines in a fan or sector as the member rotates. This is schematically shown in FIG. 10 where the transducers 54 are shown with one side connected to a common input line 72 with the other side adapted to be connected to ground 71 as the rotor rotates by the action of the saturable reactors, previously described. Only one of the transducers is connected during each 90° of rotation. The arrangement is such that as one transducer scans a 90° sector, the next transducer begins to scan the same 90° sector in sequence.

The sync generator 89 applies trigger pulses along the line 91 to an interface 92 which drives a suitable transmitter and receiver 93. For example, the transmitter-receiver may be an Ekoline 20A/B which serves to receive trigger pulses and transmit ultrasonic pulses for application to the transducer. The transducer receives the echoes from the interfaces and the receiver processes the same and provides ultrasound data along the line 94. The ultrasound data on the line 94 is applied to a data conditioning and composite video generator 96 and to a display data switch 97. At the beginning of each trigger pulse, the sync generator 89 applies a sync pulse to the sweep generator 98 which serves to form a plurality of sawtooth voltage waves such as shown in FIG. 9C. The sawtooth voltage waves provide the so-called "R" sweep voltage which is modified as will be presently described. In addition, the sync generator serves to generate a trigger pulse responsive to the output from the phototransducer 84 to thereby indicate the beginning of a sweep. This trigger pulse serves to form a sawtooth voltage such as shown in FIG. 9B which provides the $\theta$ sweep voltage which is also modified. The R and $\theta$ sweep voltages are then applied to X and Y multipliers 101 and 102 which provide outputs equal to $X = R \sin \theta$ and $Y = R \cos \theta$, respectively. This causes the sweep of the oscilloscope to be such as shown at 103 comprising a 90° scan with a plurality of scan lines 104 each beginning with the application of a pulse to the transducer and each field or scan representing 90° rotation of the transducer. The number of lines is, therefore, directly dependent upon the frequency of the ultrasonic pulses which are applied to the transducers. The ultrasound data on the line 94 is applied through the display switch to the monitor along the line 106 and serves to modulate the intensity of the beam whereby the scan will be modulated in accordance with the ultrasound data which is received as a result of reflections from the interfaces. The speed of rotation of the rotor 53 determines the number of fields or displays which are available per unit of time while the number of pulses applied determines the number of lines. It is apparent, however, that the pulse rate is limited by the depth which the scan must reach since there must be enough time between pulses to receive echoes from the deepest portion observed.

The sync signals from the sync generator 89 corresponding both to the horizontal and vertical sync signals applied to the sweep generators are also applied to a data conditioner 96. The data conditioner also receives the ultrasound data. The unit processes the data in a manner similar to a television composite signal generator. It provides a composite video signal on the line 107. The signal is illustrated at FIG. 9A and includes vertical blanking pulses 111, horizontal sync pulses 112 and the ultrasound data 113 for each scan line.

The video recorder may be any conventional video recorder such as a helical scan recorder which serves to record video signal. The rotation of the recording heads and the motion of the tape is synchronized with the timing system of the ultrasonic scanning system whereby to provide the recording of sequential fields of information.

During playback, the video recorder composite signal is applied along the line 114 to a data sync separator 116 which separates out the X and Y sync pulses and applies them to the sweep generator 98 which provides the appropriate sweep signals through the multipliers 101 and 102 for driving the deflection circuits of the cathode ray tube. The separated ultrasound data on the line 117 is applied to the display switch and directly to the video display in the same manner as the original ultrasound pulses to modulate the intensity. Thus, the playback display is identical to the original display.

What is claimed is:

1. An ultrasonic transducer probe for examining a living body comprising a rotor shaft, a rotor mounted on said shaft, a plurality of ultrasonic transducers having a transmitting and receiving face mounted on said rotor with the face directed radially outwardly therefrom, a sealed housing adapted to house said rotor and support said shaft for rotation, said housing including a thin wall adjacent the transducer face for transmitting ultrasonic energy to and from said transducers, a coupling fluid filling said housing, said fluid having an acoustic impedance corresponding generally to that of the body to be examined whereby to efficiently couple the transducer to the body, means serving to rotate said shaft and rotor so that the transducers scan through a predetermined angle, a plurality of saturable reactors one for each transducer connected in series therewith, means for mounting said saturable reactors for rotation with said shaft, and means providing a magnetic field to each of said saturable reactors as they rotate through a predetermined angle whereby the saturable reactor in the magnetic fields is saturated to lower its impedance so that it transmits electrical signals, and means connected to said saturable reactors serving to supply and receive electrical signals from the transducers associated with the saturated saturable reactor.

2. An ultrasonic transducer probe as in claim 1 including position indicating means associated with said shaft, said position indicating means associated with said shaft, said position indicating means comprising a transparent disc mounted for rotation on said shaft, a plurality of concentric opaque circles formed on said disc, said circles varying in width from a wide portion to a thin portion, a light source disposed on one side of said disc and a phototransducer disposed on the other side of said disc to receive light transmitted through the disc from the light source whereby to generate electrical signals corresponding to the light transmitted as the wide and narrow portions intercept the light.

3. An ultrasonic transducer probe for examining a living body comprising a rotor shaft, a rotor mounted on said shaft, a plurality of ultrasonic transducers having a transmitting and receiving face mounted on said rotor with the face directed radially outwardly therefrom, a sealed housing adapted to house said rotor and support said shaft for rotation, said housing including a thin wall adjacent the transducer face for transmitting ultrasonic energy to and from said transducers, a coupling fluid filling said housing, said fluid having an acoustic impedance corresponding generally to that of the body to be examined whereby to efficiently couple the transducer to the body, means serving to rotate said shaft and rotor so that the transducers scan through a predetermined angle, and position indicating means associated with said shaft, said position indicating means comprising a transparent disc mounted for rotation on said shaft, a plurality of concentric opaque circles formed on said disc, said circles varying in width from a wide portion to a narrow portion, a light source disposed on one side of said disc and a phototransducer disposed on the other side of said disc to receive light transmitted through the disc from the light source whereby to generate electrical signals corresponding to the light transmitted as the wide and narrow portions intercept the light.

4. An ultrasonic transducer probe for examining a living body comprising a rotor shaft, a rotor mounted on said shaft, a plurality of ultrasonic transducers having a transmitting and receiving face mounted on said rotor with the face directed radially outwardly therefrom, a sealed housing adapted to house said rotor and support said shaft for rotation, said housing including a thin wall adjacent the transducer face for transmitting ultrasonic energy to and from said transducers, said thin wall being at an angle with respect to the face of the transducers to minimize the effect of reflection of energy from the interface between the fluid and the window, a coupling fluid filling said housing, said fluid having an acoustic impedance corresponding generally to that of the body to be examined whereby to efficiently couple the transducer to the body, and means serving to rotate said shaft and rotor so that the transducers scan through a predetermined angle.

5. An ultrasonic transducer probe for examining a living body comprising a rotor shaft, a rotor mounted on said shaft, a plurality of ultrasonic transducers having a transmitting and receiving face mounted on said rotor with the face directed radially outwardly therefrom, a sealed housing adapted to house said rotor and support said shaft for rotation about an axis of rotation, said housing including a thin wall adjacent the transducer face for transmitting ultrasonic energy to and from said transducers, said thin wall lying on a conical surface with the center of the inner and outer surfaces of the wall on a common line coincident with the axis of rotation of the transducers whereby to minimize parallax, a coupling fluid filling said housing, said fluid having an acoustic impedance corresponding generally to that of the body to be examined whereby to efficiently couple the transducer to the body, and means serving to rotate said shaft and rotor so that the transducers scan through a predetermined angle.

6. An ultrasonic transducer probe comprising: a scanning head including a rotor shaft, a rotor mounted on said shaft, a plurality of ultrasonic transducers mounted on said rotor, a sealed housing adapted to house said rotor with one end of the shaft extending therefrom; a drive assembly including a housing for driving said shaft to rotate said rotor, said drive housing and said sealed housing including means for removably connecting said scanning head to said drive housing whereby scanning heads having desired characteristics can be interchanged with the drive; a handle associated with said drive housing to permit placement of said scanning head on a body to be examined; saturable reactors mounted to rotate with said shaft, said ultrasonic transducers having first and second terminals, a saturable reactor having one terminal connected to one terminal of each of said transducers and mounted on said support with their other terminal connected in common; means providing a magnetic field to saturate a reactor passing therethrough positioned in said housing to cooperate with each saturable reactor as it rotates therethrough; and means for applying and receiving signals between the common terminal of the saturable reactors and the other terminal of the transducers whereby the transducer associated with a saturated saturable reactor is connected to said means for applying and receiving signals.

7. An ultrasonic transducer probe as in claim 6 including a rotary transformer for coupling the common terminal of the saturable reactors and the other terminal of the transducers to means for applying signals to and receiving signals from the transducers.

8. An ultrasonic transducer probe as in claim 6 including position indicating means associated with said shaft, said position indicating means comprising a transparent disc mounted for rotation on said shaft, a plurality of concentric opaque circles formed on said disc, said circles varying in width from a wide portion to a narrow portion, a light source disposed on one side of said disc and a phototransducer disposed on the other side of said disc to receive light transmitted through the disc from the light source whereby to generate electrical signals corresponding to the light transmitted as the wide and narrow portions intercept the light.

* * * * *